United States Patent [19]

Hattendorff et al.

[11] Patent Number: 5,092,342
[45] Date of Patent: Mar. 3, 1992

[54] SENSOR ARRANGEMENT FOR OPTICALLY MEASURING GAS COMPONENTS

[75] Inventors: Horst-Dieter Hattendorff; Bernd Grabbet, both of Bad Schwartau; Eberhart Liesching, Gross Sarau; Regina Best, Lübeck, all of Fed. Rep. of Germany

[73] Assignee: Drägerwerk Aktiengesellschaft, Lübeck, Fed. Rep. of Germany

[21] Appl. No.: 533,811

[22] Filed: Jun. 6, 1990

[30] Foreign Application Priority Data

Jun. 10, 1989 [DE] Fed. Rep. of Germany ....... 3918994

[51] Int. Cl.⁵ ............................................. A61B 5/05
[52] U.S. Cl. ................................. 128/719; 250/343; 250/345
[58] Field of Search ............... 250/343, 345; 128/716, 128/719

[56] References Cited

U.S. PATENT DOCUMENTS

| | | | |
|---|---|---|---|
| 3,806,727 | 4/1974 | Leonard | 250/345 |
| 4,011,859 | 3/1977 | Frankenberger | 128/719 |
| 4,057,734 | 11/1977 | Barringer | 250/345 |
| 4,207,469 | 6/1980 | Hopkins | 250/345 |
| 4,536,090 | 8/1985 | Schmidt | 250/345 |
| 4,578,762 | 3/1986 | Wong | 128/719 |
| 4,618,771 | 10/1986 | Farren | 250/345 |
| 4,648,396 | 3/1987 | Raemer | 128/719 |
| 4,649,027 | 3/1987 | Talbot | 128/719 |
| 4,673,812 | 6/1987 | Yoneda | 250/345 |
| 4,687,337 | 8/1987 | Stewart | 250/354 |
| 4,862,001 | 8/1989 | Dowling | 250/345 |
| 4,914,720 | 4/1990 | Knodle | 128/719 |

FOREIGN PATENT DOCUMENTS 384488  11/1987  Austria ..................... 809/85

*Primary Examiner*—Ruth S. Smith
*Assistant Examiner*—Robert L. Nasser, Jr.
*Attorney, Agent, or Firm*—Walter Ottesen

[57] ABSTRACT

The invention is directed to a sensor arrangement for optically measuring the components of a gas. The sensor arrangement includes a housing containing a transmitter, a receiver device, a heatable holder for a measuring cuvette and optical devices for establishing the beam path. The sensor arrangement is improved by limiting the heating of the cuvette walls to those areas which lie in the beam path without the pass-through area of the optical devices being narrowed by the heating device. Also, the cuvette walls are heated in the manner described above without electrical contacts being disposed on the cuvette or on the sensor. The heatable cuvette holder includes one window disposed in the beam path which is transmissive for the measuring radiation. When the cuvette is seated in the cuvette holder, this window lies in virtual contact engagement with the cuvette and has a surface facing away from the cuvette. The heating device is applied to this surface of the window and is configured to allow the beam to pass therethrough.

8 Claims, 1 Drawing Sheet

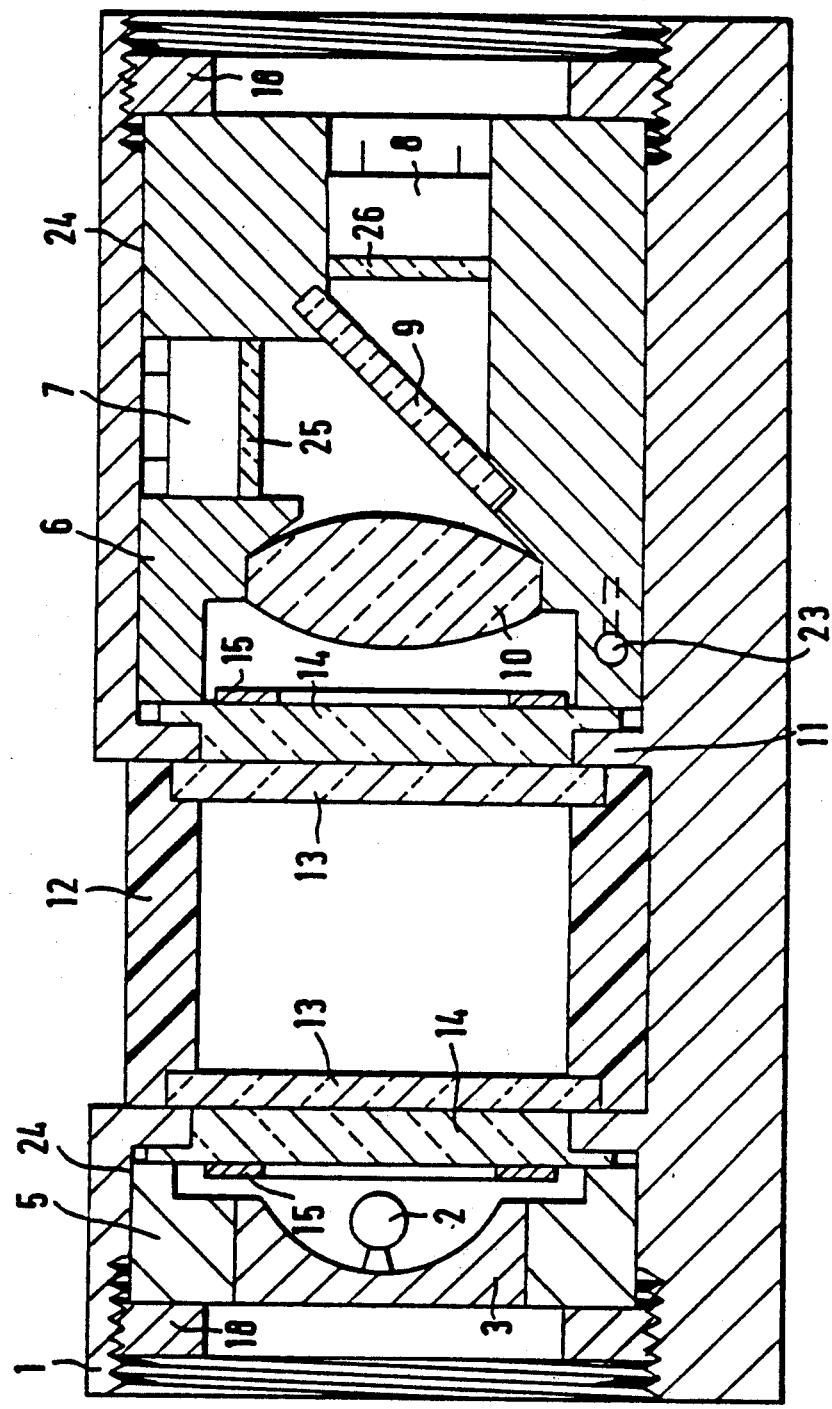

SENSOR ARRANGEMENT FOR OPTICALLY MEASURING GAS COMPONENTS

FIELD OF THE INVENTION

The invention relates to a sensor arrangement for optically measuring a gas component. The sensor arrangement includes the following: a transmitter, a receiver device, a heatable holder for a measuring cuvette and optical devices for establishing the beam path from the transmitter through the cuvette and to the receiver device.

BACKGROUND OF THE INVENTION

A sensor arrangement of the kind described above is disclosed in U.S. Pat. No. 4,011,859. The sensor arrangement disclosed in this patent measures the $CO_2$-content in a respiratory gas. The respiratory gas flows through a measuring cuvette and an infrared beam is directed through this cuvette. The radiation originates from a pulsed infrared radiation source and is focused into a beam by a lens system and the rays of the beam are directed parallel to each other through the cuvette. The infrared radiation is focused on an infrared-sensitive detector after penetrating the cuvette. The infrared radiation is more or less attenuated in correspondence to the quantity of $CO_2$ in the respiratory gas. To improve sensitivity, those wavelengths are filtered out of the infrared radiation to which the $CO_2$ molecule responds especially characteristically. This filtering is performed with the aid of an interference filter. A wavelength of approximately 4.3 micrometers is conventionally selected for this purpose.

The respiratory gas utilized in the known arrangement as a sample gas contains substantial components of water vapor which deposits on the inner walls of the cuvette. However, even when detecting other compositions of sample gas, it cannot be assumed that the gas composition is free of water vapor. Accordingly, a reduction in the transmittance of the cuvette for the beam path must be accepted in these cases when water vapor or other dirt particles deposit on the inner walls of the cuvette and especially in the transmitting region for the radiation. To prevent a condensation of water vapor in the known arrangement, the entire cuvette holder is heated and maintained at a temperature preventing the condensation. The heated cuvette holder surrounds the cuvette except for those areas which must be kept free for the pass-through of the beam through the cuvette.

The known arrangement has the disadvantage that just that area through which the beam penetrates the cuvette and again passes therefrom, can only be heated indirectly. In lieu thereof, those parts are primarily heated which are inconsequential for the beam pass-through. This results in a large thermal mass which must be brought to a constant heating temperature and maintained there by means of a corresponding amount of heat energy. Furthermore, the heat must be transported from the heated cuvette zones via heat transport in the cuvette itself to the cuvette zones penetrated by the beam.

In addition, arrangements are disclosed in Austrian Patent 384,488 wherein electrical heating elements are applied directly to the cuvette or to the cuvette window. If the cuvette is to be removable for the purpose of cleaning and disinfection or sterilization as is required, then the electrical connection of the heat elements to the sensor is provided via plug contacts. This arrangement is disadvantageous because of the tendency to mechanically malfunction through repeated insertion of the contacts and the tendency of the electrical elements on the cuvette to corrode because of the cleaning or sterilization operations. Furthermore, it may be required for certain applications such as in the area of medicine to avoid external electrical contacts which can be touched.

SUMMARY OF THE INVENTION

It is an object of the invention to provide a sensor arrangement of the kind described above which is improved so that the cuvette walls are heated only in those regions which lie in the beam path without the heating device restricting the pass-through area needed by the optical devices. It is another object of the invention to provide such a sensor arrangement wherein no heating elements are provided on the cuvette itself and where no electrical contacts are provided on the sensor which are externally accessible.

According to a feature of the invention, the cuvette holder includes at least one window which is transmissive for the measuring beam and which is located in the beam path. This window is in virtual touching contact engagement with the cuvette when the latter is seated in the sensor arrangement. A heating device is applied to the surface of the window facing away from the cuvette and allows the beam to pass through the window.

The advantage of the invention is seen essentially in that the heating device is limited to the surface of the windows to be heated and thereby makes an efficient heat transfer possible to the areas of the cuvette which are penetrated by the optical beam even though the heating originates at the cuvette holder or sensor arrangement. The heating power can be selected to be correspondingly small in order to maintain the heated area at approximately 40° C. with this heated area being small relative to the overall size of the measuring cuvette.

Because of the low required heat energy, the heating device can be an electrically conducting band formed by sputtering or vapor deposition. The electrically conductive band can be applied to the surface of a circularly-shaped window made of sapphire. The electrically conductive band is applied to a surface of this window facing away from the cuvette and is applied so as to lie outside of the beam.

According to another embodiment, the heating device can be narrow vapor deposited bands configured so as to follow a meander-shaped path or a zig-zag path. The conductive bands can extend over the entire window surface and yet leave an adequate intermediate space free for the beam to penetrate.

According to still another embodiment, the corresponding window area can be coated with an electrically conductive film which is transparent in the relevant spectral range. The heating device can also easily be embedded in the window and even so that it nearly reaches the window surface facing toward the cuvette. In each case, the presence of electrically conductive components of the heating device extending from the window surface facing toward the cuvette is to be prevented. In this way, the window in the cuvette holder or in the sensor housing itself can be enclosed in a gas-tight manner because the heating device is mounted on the surface of the window facing away from the cuvette. In this way, a hermetical separation of the gas conducting components and the electrical lines is realized. This is especially important in such cases wherein the gas to be investigated is present in explodable mixtures because if such a hermetical seal were not possible, then special reliably safe measures would have to be undertaken.

These additional safety measures are not required with the sensor arrangement of the invention.

A virtual touching engagement of the window and the cuvette is still present if an air gap of approximately 200 micrometers is present between the window and the cuvette. In this way, a good heat transfer is maintained without the necessity of accepting any significant optical losses.

The invention can be applied to sensor arrangements wherein the cuvette is transilluminated with transmitted light as well as to those embodiments wherein the beam is reflected after passing through the cuvette for the first time. Two heated windows are provided in sensor arrangements which operate pursuant to the transmitted light process and these windows lie opposite each other along the beam path. For sensor arrangements utilizing the reflective light process, a heated window as well as a second window heated in the same manner are provided in the cuvette holder or in the sensor housing. The second window is mounted closely against the mirror part of the cuvette and must not necessarily be transparent. The further description of the invention assumes that a sensor arrangement is used which operates pursuant to the transmitted light process.

A further advantage of the invention is that the two windows are separately heated and can be controlled to the desired temperature utilizing thermostat means whereby thermal dissymmetries can be compensated. Such dissymmetries occur, for example, when an infrared light source is utilized which heats both windows differently. A simple temperature control is made possible by configuring the heating device from PTC conducting tracks.

The receiver device is the component which is the most sensitive to temperature and reacts most significantly to temperature fluctuations. The detectors and optical filters of the receiver device are sensitive to temperature and this sensitivity is increased when an infrared radiation source is used as a transmitter for the measurement. The heating device is applied exclusively in direct proximity to the beam. For this reason, the closeness of the heating device to and therefore its influence on the receiving device is a very substantial advantage with respect to the temperature stability of the detectors and the optical filters.

The heated window surface can now be viewed as a contact surface for the receiver device configured as a receiver module. The receiver module is insertable into the sensor housing and can be brought into close thermal contact with the heatable window surface and aligned on the optical axis. Because of the modular-like configuration, it is on the one hand possible to provide for an optimal heat contact between the heating device and the receiver device and, on the other hand, to align the optical components and detectors built into the receiver module amongst themselves and to utilize the thermal contact surface at the same time as an optical adjustment stop. This simplifies assembly and makes possible the exchange of defective receiver modules without additional optical adjustment requirements. Furthermore, the module itself can now be manufactured exclusively of thermally good conductive material and be fitted in or inserted into the housing made of a material such as plastic which is a poor thermal conductor.

By limiting the heating device to the window surfaces, it is advantageous to provide a transmitter module which comprises the transmitter itself, an infrared radiation source for example, and a parabolic mirror reflecting the radiation emitted by the transmitter. The transmitter is likewise insertable into the housing and can be aligned with respect to the optical axis. An almost point-shaped wolfram incandescent lamp can be provided as the transmitter and is mounted in the focal point of the parabolic mirror having a small focal length of approximately 1.5 mm. The incandescent lamp and parabolic mirror conjointly define a structural unit and can be exchanged together with the module.

Both modules contain all optical elements needed for directing the radiation because the cuvette holder can define an independent unit with the heatable windows corresponding thereto. The optical adjustment complexity is significantly simplified in this manner.

It is advantageous to provide two detectors for compensating for a contamination of the cuvette surfaces penetrated by the beam. One of these detectors is sensitive to the wavelength influenced by the gas to be measured whereas the other detector is sensitive to wavelengths not influenced by the gas to be measured. The beam can be split up into the two desired wavelengths by inserting a dichroic beam splitter in the beam path ahead of the detectors. This beam splitter filters the wavelengths out of the radiation spectrum that is available, with these wavelengths being predetermined by its spectral reflection and transmission characteristics. The beam splitter directs the wavelengths to the corresponding detectors. For limiting the wavelength still further, an optical filter can be positioned ahead of the detectors. In this way, detectors are obtained which are most sensitive for detecting the different wavelengths. For this purpose, it is advantageous to equip the receiver device with the following: a lens focusing the beam passing through the cuvette; the dichroic beam splitter; the two optical filters; and, the two detectors.

The advantageous thermal coupling of the receiver device to the heating device makes it possible to provide a good temperature stabilization of the detectors, the beam splitter and the optical filters. This temperature stabilization is necessary for a precise measuring signal with the radiation symmetry which is here present. Both detectors must be maintained at precise operating temperatures which are as equal as possible in order to prevent temperature-conditioned fluctuations of the measurement signal. Measuring errors, for example caused by contamination on the cuvette windows, are eliminated by the symmetrical beam path ahead of the two detectors.

The receiver device is made of a good thermally-conductive material. The thermal stability of the receiver device is improved by configuring this device as a hollow block having an end face wherein the lens is accommodated. The hollow block has bores or recesses in which the detectors, the optical filter and the beam splitter are embedded. The components of the receiver device are now surrounded by the thermally-conductive material and insulated with respect to the ambient by the housing made of a material such as plastic which is a poor thermal conductor.

The receiver device can be thermostatically controlled by providing a temperature sensor accommodated therein. The temperature sensor is preferably embedded in the block of the receiver module. The contact surface between the receiver device and the heated window is another advantageous mounting position for the temperature sensor. In this manner, the heatable window as well as the receiver device can be controlled to a desired set temperature with one and the same temperature sensor.

The hollow block is advantageously configured so as to be cylindrical in order to make possible an axial symmetrical adjustment of the optical elements in the receiver device. A module configured in this manner can be inserted into the housing without requiring a preferred angle of rotation and can be brought into place next to the contact surface at the heated window. The same configuration can also be utilized for the transmitter module.

BRIEF DESCRIPTION OF THE DRAWING

The invention will now be described with reference to the single FIGURE of the drawing which shows a side elevation view, in section, of the sensor arrangement according to an embodiment of the invention.

DESCRIPTION OF THE PREFERRED EMBODIMENTS OF THE INVENTION

The drawing shows a sensor arrangement with which, as an example, the $CO_2$ content is detected in the respiratory air of a patient under anesthesia. For this purpose, a $CO_2$ measurement with the aid of infrared radiation is described as an example.

The sensor arrangement includes a housing 1 wherein a transmitter 2 is configured as an infrared radiation source. The radiation of the transmitter 2 is reflected at a parabolic mirror 3 which together with the transmitter 2 defines a unit. The transmitter 2 is disposed at the focal point of the parabolic mirror 3 so that the emitted infrared radiation is shaped to define a beam of essentially parallel rays. The transmitter 2 and the parabolic mirror 3 are accommodated in a cylindrically-shaped transmitter module 5 which is insertable into the housing 1. The receiver module 6 is made of metal and includes chambers wherein a measuring detector 7 and a reference detector 8 are disposed and which receive the radiation required for the measurement from a dichroic beam splitter 9. The dichroic beam splitter 9 is made of a material which preferably transmits wavelengths in the range of 3.7 micrometers, for example, and permits the rays of this wavelength range to impinge upon the reference detector 8. On the other hand, rays having a radiation wavelength in the range of 4.3 micrometers are preferably reflected and are directed to the measuring detector 7.

Interference filters (25, 26) are mounted ahead of the detectors to provide a further precise determination of the measuring and reference wavelength ranges. The $CO_2$ to be detected is sensitive to the measuring wavelength of approximately 4.3 micrometers so that the absorption of the $CO_2$ is a measure of the concentration thereof. The radiation of the reference wavelength of 3.7 micrometers is not influenced by the $CO_2$. A receiver lens 10 is built into the receiver module 6 for focusing the infrared radiation beam on the detectors (7, 8).

In the housing 1, a cuvette holder 11 is provided in the beam path between the transmitter module 5 and the receiver module 6 and a plastic cuvette 12 is inserted into the cuvette holder 11. The infrared radiation is passed through the cuvette via two cuvette windows 13. Windows 14 are seated so as to be flush with corresponding ones of the cuvette windows 13 in the cuvette holder 11. The windows 14 are transmissive for the infrared radiation and are sealed with the aid of cement or an elastomer ring.

A ring-shaped heating conductor track 15 is provided on the surface of each of the windows 14 facing away from the cuvette 12. The heating conductor track 15 operates as a heating device for the windows 14 and can be applied using thick film or thin film technology. The heating conductor tracks 15 are arranged so as to be ring-shaped and leave the pass-through opening for the mirror 3 and for the lens 10 unobstructed.

The windows 14 are made of a material having good heat conductivity such as sapphire. With the cuvette seated in place, the windows 14 are in virtual touching contact engagement with the cuvette windows 13 and so make possible a good heat transfer from the heat-conducting track 15 to the cuvette window 13. In this way, the condensation of water vapor on the inner surfaces of the cuvette windows 13 is avoided which can occur because of the moist exhaled respiratory gas in the cuvette 12.

The respiratory gas flows in via an inlet opening represented schematically by the circle 28 in the drawing and is conducted away through an outlet opening (not shown). The inlet and outlet openings lie diametrically opposite each other along an axis perpendicular to the plane of the paper of the drawing. The cylindrically-shaped modules (5, 6) are inserted into the housing 1 and lie tightly against housing 1 and are positioned so that they are in virtual contact engagement with the windows 14. Cylindrical guides 24 provide for a careful alignment of the modules (5, 6) to the optical axis of the beam path.

Threaded rings 18 provide for a firm contact engagement of the modules (5, 6), respectively. The threaded rings 18 are threadably engaged in the housing 1 and press respective ones of the modules (5, 6) against the window 14 and the cuvette holder 11. The threaded rings 18 provide a pass-through for the electrical supply of the radiation source 2 and the detectors (7, 8).

The end face of the receiver module 6 holds the receiver lens 10 and an NTC temperature sensor 23 is embedded in this end wall for temperature regulation. The measurement signals received by the detectors (7, 8) and reference signals are supplied to an evaluation unit (not shown). The evaluation unit includes a quotient circuit and generates a normalized signal from the two signals of the detectors (7, 8) by means of quotient formation and this normalized signal is a measure of the $CO_2$ contained in the cuvette 12.

It is understood that the foregoing description is that of the preferred embodiments of the invention and that various changes and modifications may be made thereto without departing from the spirit and scope of the invention as defined in the appended claims.

What is claimed is:

1. A sensor arrangement for optically measuring a gas component, the sensor arrangement comprising:
   a housing;
   a transmitter mounted in said housing for generating measuring radiation;
   first optical means also mounted in said housing for defining an optical axis and for focussing said measuring radiation into a light beam travelling down a beam path along said axis;

a receiver mounted in said housing downstream of said first optical means for receiving said beam;

light sensor means mounted in said receiver for providing a signal indicative of the intensity of the transmitted radiation of the light beam impinging thereon;

a light-transparent cuvette for accommodating the gas component to be measured;

said housing defining a cuvette holder for permitting said cuvette to be removably inserted therein while measuring the gas component;

said cuvette holder being arranged within said housing so as to hold said cuvette in said beam path between said optical means and said receiver;

said cuvette holder including window means fixedly mounted in said housing so as to be in said beam path for passing said beam to said cuvette wherein the gas component to be detected affects the intensity of said light beam;

said window means being positioned in said housing so as to cause said cuvette to be in virtual contact engagement with said window means when said cuvette is seated in said holder;

said window means having a first side in said virtual contact engagement with said cuvette and a second side facing away from said cuvette;

heating means mounted on said second side for heating said window means and transferring heat to said cuvette;

said heating means being arranged on said second side so as to permit said beam to pass unobstructed through said window means and to said cuvette; and, second optical means for directing said light beam onto said light sensor means after said light beam has passed through the gas in said cuvette.

2. The sensor arrangement of claim 1, said receiver being configured as a module removably inserted into said housing so as to lie on said axis and be in close thermal contact to said second side of said window means.

3. The sensor arrangement of claim 1, said first optical means including a parabolic mirror for reflecting and focussing said measuring radiation to form said beam; and, said transmitter and said parabolic mirror conjointly defining a transmitter module removably inserted into said housing for positioning said optical axis.

4. The sensor arrangement of claim 1, said second optical means being mounted in said receiver and including: a lens for focussing the beam passing through said cuvette; and, a dichroic beam splitter disposed downstream of said lens for splitting said beam into two component beams; and, said light sensor means including a reference sensor for receiving one of said component beams; a measuring sensor for receiving the other one of said component beams; and, said sensors being made sensitive to detect different wavelengths.

5. The sensor arrangement of claim 4, said receiver including: a block made of metal and having a wall defining a hollow formed therein; said block having an end face for accommodating said lens therein; and, said sensors being recessed in said wall.

6. The sensor arrangement of claim 5, said block having a cylindrical configuration.

7. The sensor arrangement of claim 1, wherein said sensor arrangement further comprises a temperature sensor accommodated in said receiver.

8. A sensor arrangement for optically measuring a gas component, the sensor arrangement comprising:

a housing;

a transmitter mounted in said housing for generating measuring radiation;

first optical means also mounted in said housing for defining an optical axis and for focussing said measuring radiation into a light beam travelling down a beam path along said axis;

a receiver mounted in said housing downstream of said optical means for receiving said beam;

light sensor means mounted in said receiver for providing a signal indicative of of the intensity of the transmitted radiation of the light beam impinging thereon;

a light-transparent cuvette for accommodating the gas component to be measured;

said housing defining a cuvette holder for permitting said cuvette to be removably inserted therein while measuring the gas component;

said cuvette holder being arranged within said housing so as to hold said cuvette in said beam path between said first optical means and said receiver;

said cuvette holder including a first window fixedly mounted in said housing so at to be in said beam path for passing said beam to said cuvette wherein the gas component to be detected affects the intensity of the light of said light beam;

said cuvette holder including a second window fixedly mounted in said housing for passing said light beam from said cuvette to said receiver;

said windows being positioned in said housing so as to cause said cuvette to be in virtual contact engagement with said windows when said cuvette is seated in said holder;

each of said windows having a first side in said virtual contact engagement with said cuvette and a second side facing away from said cuvette;

heating means mounted on the second side of each of said windows for heating the window and transferring heat to said cuvette;

said heating means being arranged on the second side of each of said windows so as to define a clear unobstructed region to permit said beam to pass therethrough; and, second optical means for directing said light beam onto said light sensor means after said light beam has passed through the gas in said cuvette.

* * * * *

UNITED STATES PATENT AND TRADEMARK OFFICE
CERTIFICATE OF CORRECTION

PATENT NO. : 5,092,342

DATED : March 3, 1992

INVENTOR(S) : Horst-Dieter Hattendorff, Bernd Grabbet, Eberhart Liesching and Regina Best It is certified that error appears in the above-identified patent and that said Letters Patent is hereby corrected as shown below:

In column 8, line 25: delete "of" (first occurrence).

In column 8, line 37: delete "at" and substitute -- as -- therefor,

Signed and Sealed this

Fifteenth Day of June, 1993

Attest:

MICHAEL K. KIRK

Attesting Officer

Acting Commissioner of Patents and Trademarks